United States Patent
Hwu et al.

Patent Number: 6,121,255
Date of Patent: Sep. 19, 2000

[54] PHLOROGLUCIDE DERIVATIVES AND THEIR PHARMCEUTICAL USE

[75] Inventors: Jih Ru Hwu; Shwu-Chen Tsay; Gholam H. Hakimelahi; Chun Chieh Lin, all of Taipei; Wen Nan Tseng, Hsinchu, all of Taiwan; Ali A. Moshfegh, Shiraz, Islamic Rep. of Iran; Abdolmajid Azaripour, Shiraz, Islamic Rep. of Iran; Hasan Mottaghian, Shiraz, Islamic Rep. of Iran

[73] Assignee: National Science Council, Taiwan

[21] Appl. No.: 09/072,191

[22] Filed: May 4, 1998

[51] Int. Cl.$^7$ ............... A61K 31/545; C07D 501/26; C07D 501/28; C07C 69/94; C07C 65/40

[52] U.S. Cl. ............... 514/200; 540/215; 540/230; 560/52; 560/57; 562/460; 562/468; 564/169; 564/171; 514/209

[58] Field of Search .................. 514/200, 209; 540/230, 215

[56] References Cited

PUBLICATIONS

Jih Ru Hwu, Ali A. Moshfegh, Shwu-Chen Tsay, Chun Chieh Lin, Wen Nan Tseng, Abdolmajid Azaripour, Hasan Mottaghian and Gholam H. Hakimelahi, "Cephalosporin 3'-Phloroglucide Esters and 7-(Phloroglucidamido) cephalosporins as Novel Antibacterial Agents,"J. Med. Chem. 1997 (Sep.), pp. 40, 3434–3441.

*Primary Examiner*—Mark L Berch
*Attorney, Agent, or Firm*—Hitt Chwang & Gaines, P.C.

[57] ABSTRACT

A phloroglucide derivative having the following formula:

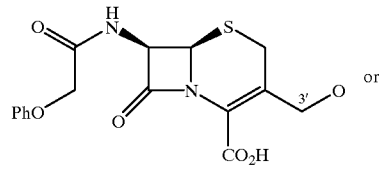
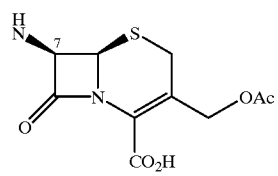

wherein Q is halogen; X is $CH_2$ or C=O; Y is cephalosporin having a formula of (I)

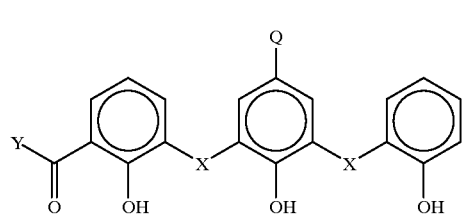

wherein Ph is phenyl, Ac is acetoxy, or pharmaceutically acceptable salts thereof, and an antibacterial pharmaceutical composition derived thereof.

8 Claims, No Drawings

PHLOROGLUCIDE DERIVATIVES AND THEIR PHARMCEUTICAL USE

FIELD OF THE INVENTION

The present invention is related generally to synthesis of novel phloroglucide derivatives and their pharmaceutical use, and more particularly to synthesis of novel phloroglucide derivatives which possess potent antibacterial activities. They include unsymmetrical phloroglucide analogs, phloroglucides attached to cephalosporins at the C-3'position, and 7-(phloroglucidamido)cephalosporins.

BACKGROUND OF THE INVENTION

The presence of essential functional groups with a suitable spatial arrangement for chelation with metal ions of enzymes is a significant feature common to several classes of antibiotics [Moshfegh, A. et al. *Helv. Chim. Acta* 1957, 40, 1157]. They include trisaspidinol [Widen, C.-J. et al. *Helv. Chim. Acta* 1973, 56, 831], cryptosporin [Closse, A. et al. *Helv. Chim. Acta* 1973, 56, 619], and tetracycline [Albert, A. *Nature (London)* 1953, 172, 201]. These compounds exhibit various degrees of activity against Gram-positive bacteria as well as other microorganisms. It was reported that the presence of halogen atoms in phloroglucide analogs is essential for their antibacterial activity [Hakimelahi, G. H. et al. *Helv. Chim. Acta* 1981, 64, 599; Swiss Patent 003848, 1977; Swiss Patent 003849, 1977; Swiss Patent 007448, 1978. Moshfegh, A. A. et al. *Helv. Chim. Acta* 1982, 65, 1221; *Helv. Chim. Acta* 1982, 65, 1229; *Helv. Chim. Acta* 1982, 65, 1264].

β-Lactam antibiotics exert certain biological activity by acylating serine residues of transpeptidases, in which the cross-linking of peptidoglycans does not take place [Waxman, D. J. et al. *J. Biol. Chem.* 1980, 255, 3964]. The ring opening of the β-lactamase nucleus would occur when cephalosporins react with bacterial enzymes. Consequently, the substituent attached at the C-3'position is liberated. When the eliminated species possesses antibacterial activity, cephalosporins would exhibit a dual mode of action [O'Callaghan, C. H. et al. *Antimicrob. Agents Chemother.* 1976, 10,245; Greenwood, D. et al. *Antimicrob. Agents Chemother.* 1976, 10, 249; Beskid, G. et al. *Chemotherapy* 1990, 36, 109]. It was reported that attachment of antibacterial quinolones to the C-3'position of cephalosporins gives a class of new compounds with a broadened spectrum of antibacterial activities [Albrecht, H. A. et al. *J. Med. Chem.* 1990, VI, 77; *J. Med. Chem.* 1991, 34, 669; *J. Med. Chem.* 1994, 37, 400].

SUMMARY OF THE INVENTION

The present invention discloses a novel class of phloroglucide derivatives, including unsymmetrical phloroglucide analogs, phloroglucides attached to cephalosporins at the C-3'position, and 7-(phloroglucidamido)cephalosporins as antibacterial agents. They exhibited more potent antimicrobial activity than the previous reported phloroglucide derivatives.

The characteristics of this invention is that cephalosporin 3'-phloroglucide esters, which were obtained by condensation of cephalosporin with bioactive phloroglucides, exhibited a dual mode of antibacterial activity in vitro. In comparison with traditional cephalosporins bearing an acetoxy unit at the C-3'position, the bifunctional cephalosporins showed a broadened spectrum of activity.

Unlike cephalosporin 3'-phloroglucide esters, 7-(phloroglucidamido)cephalosporins were found resistant to β-lactamases from *Staphylococcus aureus* 95 and *Pseudomonas aeruginosa* 18S-H. These new compounds, however, showed notable activities against *Staphylococcus aureus* FDA 209P, *Staphylococcus aureus* 95, *Candida albicans*, *Pseudomonas aeruginosa* 1101–75, and *Pseudomonas aeruginosa* 18S-H. In this invention, new phloroglucide derivatives are disclosed as potent antibacterial agents. They have a high potential in the development of new antibacterial drugs.

DETAILED DESCRIPTION OF THE INVENTION

The present invention discloses a novel phloroglucide derivative having the following formula:

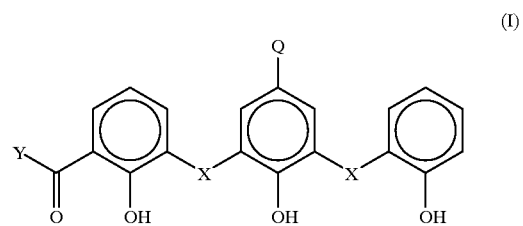

Where Q is halogen; X is $CH_2$ or C=O; Y is hydroxyl, methoxy, $NH(CH_3)$ or cephalosporin having formulas as follows:

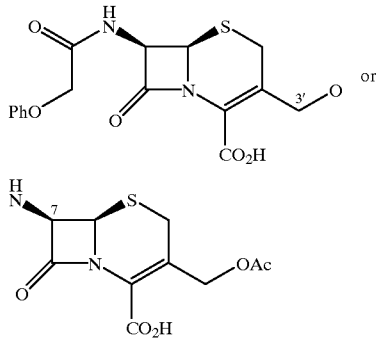

wherein Me is methyl, Ph is phenyl, Ac is acetoxy, or pharmaceutically acceptable salts thereof.

Preferably, X of the phloroglucide derivative of formula (I) is $CH_2$.

Preferably, Y of the phloroglucide derivative of formula (I) is

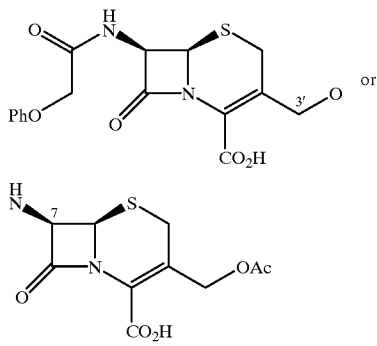

The present invention may provide a method for the use of antibacterial drugs. In the preferred embodiments of the present invention, the following compounds (II) to (XI) were synthesized. The compounds (II) to (VII) are unsymmetrical phloroglucides, and the compounds (VIII) to (XI) are cephalosporin-phloroglucide derivatives.
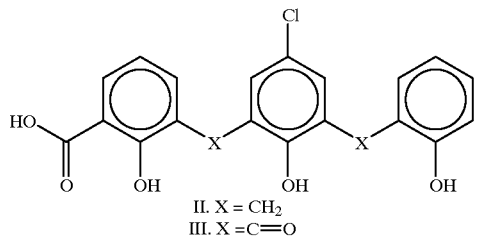
II. X = CH$_2$
III. X = C=O
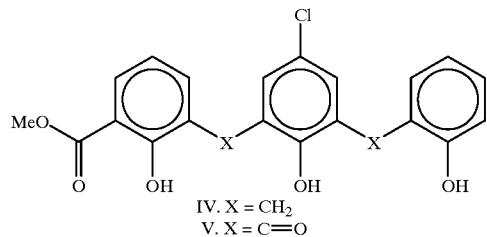
IV. X = CH$_2$
V. X = C=O
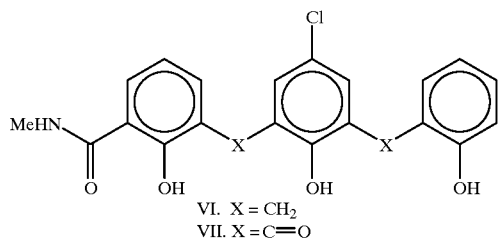
VI. X = CH$_2$
VII. X = C=O
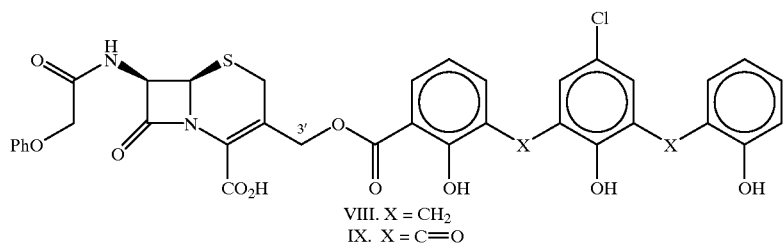
VIII. X = CH$_2$
IX. X = C=O
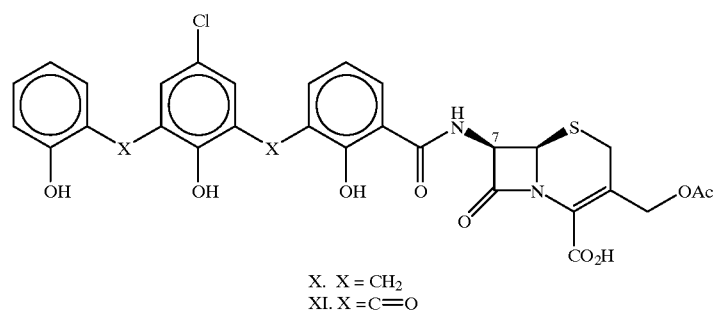
X. X = CH$_2$
XI. X = C=O
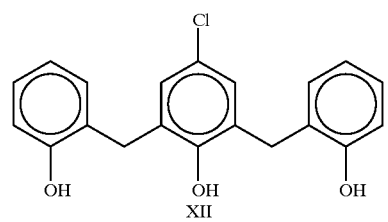
XII

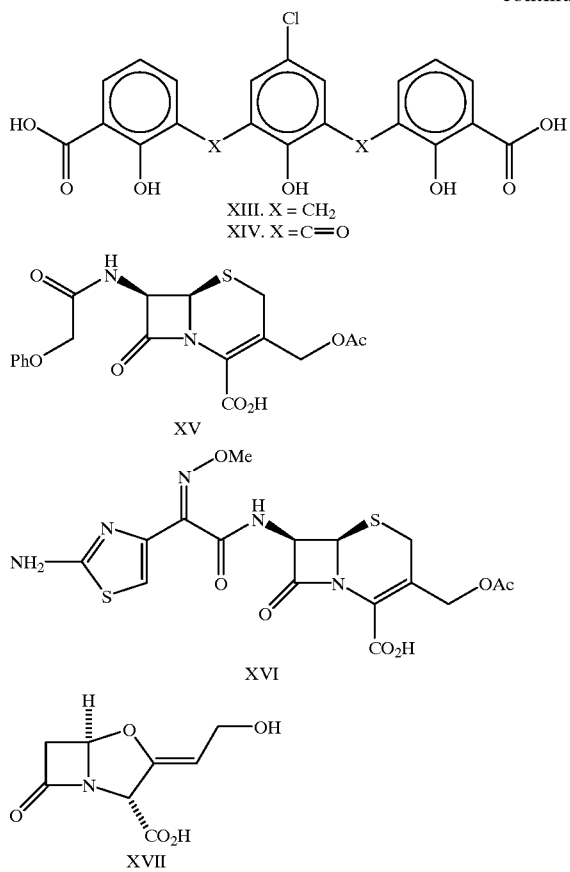

XIII. X = CH₂
XIV. X = C=O

XV

XVI

XVII

Compound (II) having one carboxylic acid unit at the C-3'position exhibited more potent antimicrobial activity than that of the model phloroglucide (XII). When the methylene bridges in phloroglucide (II) were converted to carbonyl functionalities as in the phenolic keto acid (III), its antimicrobial property decreased. In comparison with dicarboxylic acid derivative (XIV), mono-carboxylic acid (II) however exhibited greater potency. Phenolic keto acid (III, however, showed a lower efficacy than phenolic acid (II) and phenol (XII) against pathogenic microorganisms.

In comparison with the reference cephalosporins (XV) and (XVI), cephemphloroglucidic esters (VIII) and (DC possessed a broadened spectrum of antibacterial activity in vitro. On the other hand, (VIII) and (IX) showed greater antibacterial activity than the corresponding phloroglucides (II) and (III) against S. aureus FDA 209P, yet less activity against other pathogenic microorganisms. Nevertheless, the activity added to the spectrum of the parent cephalosporin parallels the activity of the phloroglucide component in each assay.

The antibacterial activity of simple esters (IV) and (V) as well as the corresponding amides (VI) and (VII) exhibited lower efficacy than phloroglucides (II) and (II) as well as the bifunctional cephalosporins (VIII) and (IX). Compounds (VIII) and (IX) are dual-action antibiotics; their biological activities came from both phloroglucide and cephalosporin moieties. This pattern of activity reveals that the corresponding phloroglucides (II) and (III) were released in situ from bifunctional cephalosporins (VIII) and (IX), respectively.

On the other hand, 7-(phloroglucidamido)cephalosporins (X) and (XI) are not expected to exhibit a dual mode of action, yet they showed notable antibacterial activity. Compound (X) exhibited potent phloroglucide-like antibacterial activity.

Results from the biological assay, cephalosporin-phloroglucide esters (VIII) and (IX) underwent hydrolysis to liberate their phloroglucide components, as evidenced by their notable values of minimum protective concentration (MPC) against the β-lactamases of S. aureus 95 and Ps. aeruginosa 18S-II. Therefore, cephemphloroglucidic esters (VIII) and (IX) exhibited phloroglucide-like antibacterial activity. Reference cephalosporins (XV) and (XVI) were also susceptible to hydrolysis by β-lactamases. As a result, they did not show significant activity against β-lactamase producing microorganisms (i.e., S. aureus 95). 7-(Phloroglucidamido)cephalosporins (X) and (XI) did not exhibit notable β-lactamase inhibitory property. Thus their pronounced antimicrobial activity is mainly due to their stability towards β-lactamases.

The invention will be further illustrated by the following examples which are only meant to illustrate the invention, but not to limit it. The reaction routes for synthesizing the title compounds of the Preparation Examples 1–5, 6–9, and 10–13 are shown in the Schemes 1, 2, and 3, respectively.

Scheme 1
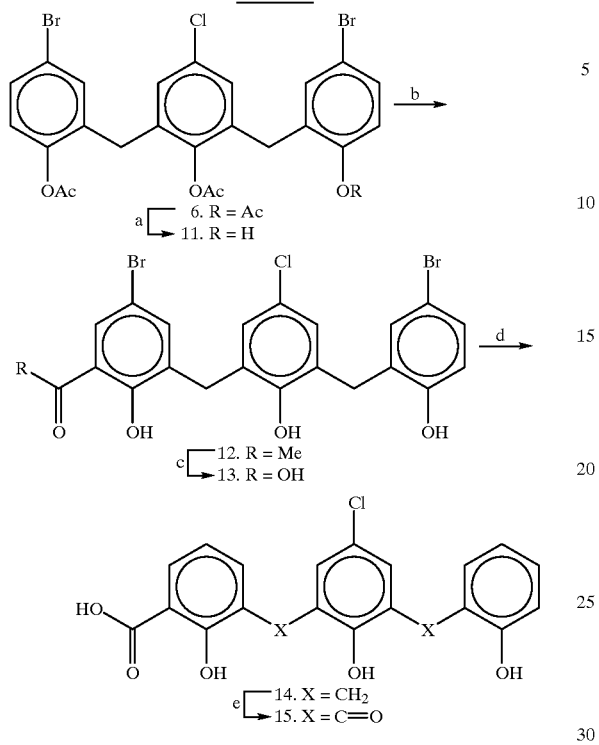
Reagents: (a) NaOH, THF; (b) AlCl₃; (c) 1. NaCl; (d) Zn, KOH(aq); (e) 1. Ac₂O, 2. CrO₃, 3. NaOH, 4. HCl.
Scheme 2
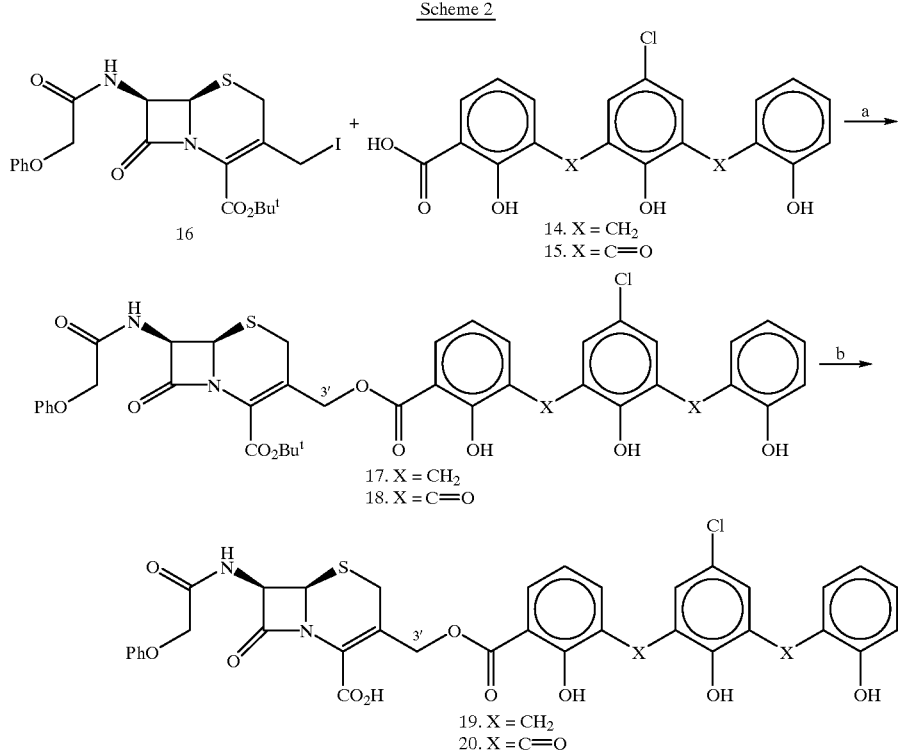
Reagents: (a) NaHCO₃, DMF; (b) CF₃CO₂H, CH₂Cl₂.

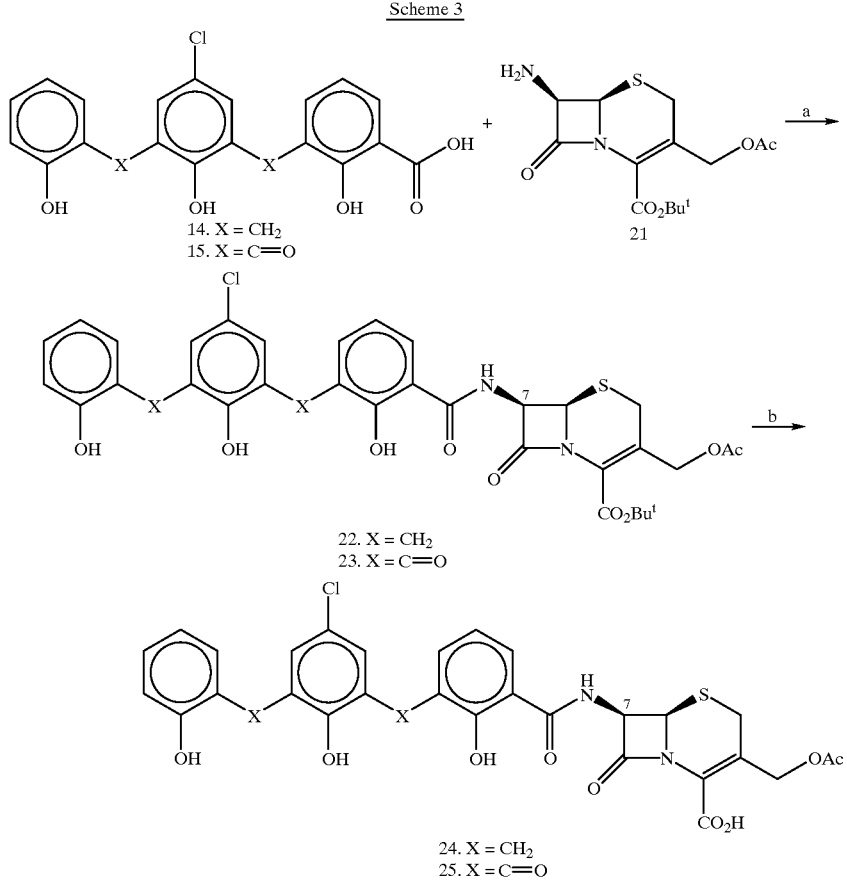

Scheme 3

Reagents: (a) 1. Me₃SiNHSiMe₃, (NH₄)₂SO₄(cat.),2. EEDQ, THF; (b) CF₃CO₂H, CH₂Cl₂.

PREPARATION EXAMPLE 1

2-Acetoxy-1-(2-acetoxy-5-bromobenzyl)-3-(5-bromo-2-hydroxybenzyl)-5-chlorobenzene (11)

To a solution of 6 (6.12 g, 9.80 mmol) in THF (70 mL) was added 1% aqueous solution of NaOH (0.39 g, 9.75 mmol) at 0° C. within 30 min. The reaction mixture was stirred at the same temperature for 1.0 h and then was allowed to stand at room temperature for 1.5 h. After evaporation of THF and acidification with 10% aqueous HCl solution (12 mL), phenol 11 (5.60 g, 9.60 mmol) was recrystallized from EtOH as a white crystal in 98% yield: mp 190–192° C.; $^1$H NMR (DMSO-$d_6$/ $D_2$O) d 2.26(s, 6H, 2×CH₃), 3.61 (s,4H, 2×CH₂), 6.92–7.35 (m, 8H, 3×ArH); IR (CH₂Cl₂): 3300–3350 (OH), 1740 esters cm$^{-1}$. Anal. ($C_{24}H_{19}Br_2ClO_5$) C, H, Br, Cl.

PREPARATION EXAMPLE 2

2-(3-Acetyl-5-bromo-2-hydroxybenzyl)-6-(5-bromo-2-hydroxybenzyl)-4-chlorophenol (12)

Compound 12 (3.78 g, 6.99 mmol) was prepared in 70% yield from 11 (5.82 g, 9.99 mmol) and AlCl₃(15.0 g, 112 mmol) by the method used for the synthesis of 7 from 6. For 12: mp 185–186° C.; $^1$H NMR (DMSO-$d_6$/$D_2$O) d 2.18 (s, 3H, CH₃), 3.60(br s, 4H,2×CH₂), 7.03–7.32(m, 7H, 3×ArH); IR (KBr): 3300–3400(OH), 1650(C=O), 1169, 1360, 1210, 780 cm$^{-1}$. Anal. ($C_{22}H_{17}Br_2ClO_4$) C, H, Br, Cl.

PREPARATION EXAMPLE 3

2-(5-Bromo-3-carboxy-2-hydroxybenzyl)-6-(5-bromo-2-hydroxybenzyl)-4-chlorophenol (13)

Compound 13 (5.15 g, 9.49 mmol) was synthesized in 95% yield from 12 (5.40 g, 9.99 mmol) by the same method used for the preparation of 8 from 7. For 13: mp 200° C. (dec.); $^1$H NMR (DMSO-$d_6$D₂O) d 3.61 (br s, 4H, 2×CH₂), 6.65–7.30 (m, 7H, 3×Ar IR (KBr): 3250–3500 (OH, CO₂H), 1626 (C=O), 1215,990 cm$^{-1}$. Anal. ($C_{21}H_{15}Br_2ClO_5$)C, H, Br, Cl.

PREPARATION EXAMPLE 4

2-(3-Carboxy-2-hydroxybenzyl)-6-(2-hydroxybenzyl)-4-chlorophenol (14)

Compound 14 (3.34 g, 8.69 mmol) was prepared in 87% yield from 13 (5.42 g, 9.99 mmol), 40% KOH solution (50 mL), and Zn dust (5.00 g, 76.5 mmol) by the same method used for the synthesis of 9 from 8. Compound 14 was sublimed at 160–165° C. under 0.03 torr: mp 198–200° C.; $^1$H NMR (DMSO-$d_6$/D₂O) d 3.60 (s, 4H, 2×CH₂), 6.84–7.29 (m, 9H, 3×ArH); IR (KBr): 3300–3500 (OH, CO₂H), 1620 (C=O), 1211, 994 cm$^{-1}$; MS m/z384 (M⁺, Cl-clusters). Anal. ($C_{21}H_{17}ClO_5$) C, H, Cl.

PREPARATION EXAMPLE 5

2-(3-Carboxy-2-hydroxybenzoyl)-6-(2-hydroxybenzoyl)-4-chlorophenol (15)

Compound 15 (1.50 g, 3.64 mmol) was prepared from 14 (1.92 g, 4.99 mmol) in 73% yield by the same method used for the synthesis of 10 from 9. For 15: mp 127–130° C.; $^1$H NMR (DMSO-d$_6$,D$_2$O) d 6.70–7.49 (m, 9H, 3×ArH); IR (KBr): 3210–3430 (OH, CO$_2$H), 1610–1630(C=O), 1169, 1600, 1495, 1210, 995 cm$^{-1}$; MS m/z 412 (M$^+$, Cl-clusters). Anal. (C$_{21}$H$_{13}$ClO$_7$) C, H, Cl.

PREPARATION EXAMPLE 6 tert-Butyl 3-{3-[5-Chloro-2-hydroxy-3-(2-hydroxybenzyl)benzyl]-2-hydroxybenzoyloxymethyl}7-phenoxyacetamido-3-cephem-4-carboxylate (17)

A solution of 16 (5.30 g, 9.99 mmol), 14(3.86 g, 10.0 mmol), and NaHCO$_3$(2.52 g, 30.0 mmol) in DMF (150 mL) was stirred under N$_2$ for 4.0 h. The solvent was evaporated under reduced pressure and the residue was taken up in EtOAc (200 mL) and washed with 1% aqueous HCl solution (100 mL) and water (150 mL). The organic layer was dried over MgSO$_4$ (s), filtered, and evaporated. Purification by use of silica gel column chromatography with EtOAc as the eluant afforded 17 (7.57 g, 9.50 mmol) as a white crystal in 95% yield: mp 155–157° C.; $^1$H NMR (DMSO-d$_6$) d 1.49 (s, 9H, 3×CH$_3$), 3.61 (br s, 4H, 2×CH$_2$), 3.70, 3.80 (AB, J$_{gem}$=19 Hz, 2H, CH$_2$S), 4.63 (s, 2H, OCH$_2$CO), 4.86, 5.10 (AB, J$_{gem}$=14 Hz, 2H, CH$_2$O), 5.17 (d, J=4.9Hz, 1H, HC(6)), 5.77(dd, J=4.9 and 8.5 Hz, 1H, HC(7)), 6.60–7.35 (m, 18H, NH+3×OH+4×ArH); IR (nujol): 3300–3400 (OH, NH), 1790 (β-lactam), 1745 (ester), 1725 (ester), 1680 (amide) cm$^{-1}$. Anal. (C$_{41}$H$_{39}$N$_2$O$_{10}$SCl) C, H, N, S, Cl.

PREPARATION EXAMPLE 7 tert-Butyl 3-{3-[5-Chloro-2-hydroxy-3-(2-hydroxybenzoyl)benzyl]-2-hydroxybenzoyloxymethyl}-7-phenoxyacetamido-3-cephem-4-carboxylate (18)

Compound 18 (7.33 g, 8.99 mmol) was prepared from 16 (5.30 g, 9.99 mmol), 15 (4.13 g, 10.0 mmol), and NaHCO$_3$ (2.52 g, 30.0 mmol) in 90% yield by the same method used for the preparation of 17. For 18: mp 138–140° C.; $^1$H NMR (DMSO-d$_6$) d 1.50 (s, 9H, 3×CH$_3$), 3.72, 3.83 (AB, J$_{gem}$=19 Hz, 2H, CH$_2$S), 4.60 (s, 2H, OCH$_2$CO), 4.99, 5.29 (AB, J$_{gem}$=15 Hz, 2H, CH$_2$O), 5.18 (d, J=5.0 Hz, 1H, HC(6)), 5.79 (dd, J=5.0 and 9.5 Hz, 1H, HC(7)), 6.20 (br, 3H, 3×OH), 6.90–7.50 (m, 14H, 4×ArH), 8.30 (d, J=9.5 Hz, 1H, NH); IR (nujol): 3290–3370 (OH, NH), 1792 (β-lactam), 1750 (ester), 1730 (ester), 1688 (amide), 1620 (C=O) cm$^{-1}$. Anal. (C$_{41}$H$_{35}$N$_2$O$_{12}$SCl) C, H, N, S, Cl.

PREPARATION EXAMPLE 8

3-{3-[5-Chloro-2-hydroxy-3-(2-hydroxybenzyl)benzyl]-2-hydroxy-benzoyloxymethyl}-7-phenoxyacetamido-3-cephem-4-carboxylic Acid (19)

A solution of 17 (3.93 g, 4.99 mmol) in CF$_3$CO$_2$H (35%) in CH$_2$Cl$_2$ (45 mL) was stirred at room temperature for 13 h. The solution was condensed under reduced pressure and then CCl$_4$ (30 mL) was added to the residue and evaporated. The resultant solid was crystallized from a mixture of EtOH and ether (2:1) to afford pure 19 (3.28 g, 4.49 mmol) as a white crystal in 90% yield: mp 196–198° C.; $^1$H NMR (DMSO-d$_6$/D$_2$O) d 3.60 (br s, 4H, 2×CH$_2$), 3.68, 3.79 (AB, J$_{gem}$=19 Hz, 2H, CH$_2$S), 4.65 (s, 2H, OCH$_2$CO), 4.95, 5.21 (AB, J$_{gem}$=14 Hz, 2H, CH$_2$O), 5.15 (d, J=5.1 Hz, 1H, HC(6)), 5.76 (d, J=5.1 Hz, 1H, HC(7)), 6.80–7.35 (m, 14H, 4×ArH); IR (nujol): 3300–3450 (OH, NH, CO$_2$H), 1785 (β-lactam), 1720 (ester), 1685 (amide), 1610 (C=O) cm$^{-1}$. Anal. (C$_{37}$H$_{31}$N$_2$O$_{10}$SCl) C, H, N, S Cl.

PREPARATION EXAMPLE 9

3-{3-[5-Chloro-2-hydroxy-3-(2-hydroxybenzoyl)benzoyl]-2-hydroxybenzoyloxymethyl}-7-phenoxyacetamido-3-cephem-4-carboxlic Acid (20)

Compound 20 (3.21 g, 4.23 mmol) was prepared from 18 (3.66 g, 4.49 mmol) in 94% yield by the method used for the preparation of 19. For 20: mp 180–182° C.; $^1$H NMR (DMSO-d$_6$/D$_2$O) d 3.69, 3.81 (AB, J$_{gem}$=19 Hz, 2H, CH$_2$S), 4.61 (s, 2H, OCH$_2$CO), 4.93, 5.20 (AB, J$_{gem}$=14 Hz, 2H, CH$_2$O), 5.20 (d, J=5.0 Hz, 1H, HC(6)), 5.77 (d, J=5.0 Hz, 1H, HC(7)), 6.96–7.53 (m, 14H, 4×ArH); IR (nujol): 3270–3400 (OH, NH, CO$_2$H)), 1788 (β-lactam), 1725 (ester), 1680 (amide), 1620–1635 (C=O) cm$^{-1}$. Anal. (C$_{37}$H$_{27}$N$_2$O$_{12}$SCl) C, H, N, S, Cl.

PREPARATION EXAMPLE 10 tert-Butyl 7-{3-[5-Chloro-2-hydroxy-3-(2-hydroxybenzyl)benzyl]-2-hydroxybenzamido}cephalosporanate (22)

To a suspension of compound 14 (1.67 g, 4.34 mmol) in 1,1,1,3,3,3-hexamethyldisilazane (50 mL) was added ammonium sulfate (0.300 g, 2.27 mmol). The reaction mixture was heated at reflux for 5.0 h. The solvent was evaporated and the residue was dissolved in dry THF (40 mL). β-Lactam 21 (1.44 g, 4.39 mmol) and 2-ethoxy-1-ethoxycarbonyl-1,2-dihydroquinoline (1.23 g, 4.97 mmol) were then added and the solution was stirred at room temperature for 24 h. It was then partitioned between EtOAc (100 mL) and 3% aqueous HCl solution (70 mL). The organic layer was washed with water (100 mL), dried over MgSO$_4$ (s), filtered, and condensed. Purification by use of silica gel column chromatography with EtOAc as eluant gave 22 (2.41 g, 3.47 mmol) as a white crystal in 80% yield: mp 147–149° C.; $^1$H NMR (DMSO-d$_6$) d 1.50 (s, 9H, 3∞CH$_3$), 2.22 (s, 3H, CH$_3$CO), 3.59 (br s, 4H, 2×CH$_2$), 3.69, 3.80 (AB, J$_{gem}$=18 Hz, 2H, CH$_2$S), 4.80, 5.22 (AB, J$_{gem}$=13 Hz, 2H, CH$_2$O), 5.20 (d, J=5.1 Hz, 1H, HC(6)), 5.86 (dd, J=5.1 and 10 Hz, 1H, HC(7)), 6.58 (br, 3H, 3×OH), 6.89–7.40 (m, 9H, 3×ArH), 9.20 (d, J=10 Hz 1H, NH); IR (nujol): 3300–3350 (NH, OH), 1785 (β-lactam), 1750 (ester), 1735 (ester), 1655 (amide) cm$^{-1}$. Anal. (C$_{35}$H$_{35}$N$_2$O$_9$SCl) C, H, N, S, Cl.

PREPARATION EXAMPLE 11 tert-Butyl 7-{3-{5-Chloro-2-hydroxy-3-(2-hydroxybenzoyl)benzoyl}-2-hydroxybenzamido}cephalosporanate (23)

Compound 23 (2.76 g, 3.82 mmol) was prepared in 88% yield from 21 (1.44 g, 4.39 mmol) and 15 (1.79 g, 4.34 mmol) by the method used for the preparation of 22 from 21 and 14. For 23: mp 136–138° C.; $^1$H NMR (DMSO-d$_6$) d 1.48 (s, 9H, 3∞CH$_3$), 2.23 (s, 3H, CH$_3$CO), 3.70, 3.81 (AB, J$_{gem}$=19 Hz, 2H, CH$_2$S), 4.82, 5.29 (AB, J$_{gem}$=13 Hz, 2H, CH$_2$O), 5.10 (d, J=4.9 Hz, 1H, HC(6)), 5.90 (dd, J=4.9 and 9.5 Hz, 1H, HC(7)), 6.90–7.50 (m, 12H, 3×OH+3×ArH), 9.50 (d, J=9.5 Hz, NH); IR (nujol): 3250–3350 (NH, OH), 1790 (β-lactam), 1750 (ester), 1735 (ester), 1656 (amide), 1625 (C=O) cm$^{-1}$. Anal. (C$_{35}$H$_{31}$N$_2$O$_{11}$SCl) C, H, N, S, Cl.

PREPARATION EXAMPLE 12

7-{3-[5-Chloro-2-hydroxy-3-(2-hydroxybenzyl)benzyl]-2-hydroxybenzamido}cephalosporanic Acid (24)

Compound 24 (1.77 g, 2.77 mmol) was synthesized in 83% yield from 22 (2.32 g, 3.33 mmol) by the method used for the synthesis of 19 from 17. For 24: mp 189–192° C.; $^1$H NMR (DMSO-d$_6$/D$_2$O) d 2.23 (s, 3H, CH$_3$CO), 3.60 (br s, 4H, 2×CH$_2$), 3.70, 3.81 (AB, J$_{gem}$=19 Hz, 2H, CH$_2$S), 4.81, 5.22 (AB, J$_{gem}$=13 Hz, 2H, CH$_2$O), 5.21 (d, J=4.9 Hz, 1H, HC(6)), 5.80 (d, J=4.9 Hz, 1H, HC(7)), 6.90–7.39 (m, 9H, 3×ArH); IR(nujol): 3260–3400 (NH, OH, CO$_2$H), 1780 (β-lactam), 1730 (ester), 1650 (amide), 1615 (C=O) cm$^{-1}$. Anal. (C$_{31}$H$_{27}$N$_2$O$_9$SCl) C, H, N, S, Cl.

PREPARATION EXAMPLE 13

7-{3-[5-Chloro-2-hydroxy-3-(2-hydroxybenzoyl) benzoyl]-2-hydroxybenzamido}cephalosporanic Acid (25)

Compound 25 (1.02 g, 1.53 mmol) was prepared in 80% yield from 23 (1.38 g, 1.91 mmol) by the method used for the preparation of 20 from 18. For 25: mp 173–175° C.; $^1$H NMR (DMSO-d$_6$/D$_2$O) d 2.22 (s, 3H, CH$_3$CO), 3.68, 3.79 (AB, J$_{gem}$=19 Hz, 2H, CH$_2$S), 4.80, 5.20 (AB, J$_{gem}$=13 Hz, 2H, CH$_2$O), 5.20 (d, J=5.1 Hz, 1H, HC(6)),5.85 (d, J=5.1 Hz, 1H, HC(7)), 6.90–7.40 (m, 9H, 3×ArH); IR (nujol): 3250–3400 (NH, OH, CO$_2$H), 1785 (β-lactam), 1730 (ester), 1652 (amide), 1615–1625 (C=O) cm$^{-1}$. Anal (C$_{31}$H$_{23}$N$_2$O$_{11}$SCl) C, H, N, S, Cl.

EXAMPLE 1

Determination of Minimum Inhibitory Concentrations of Phloroglucide and Cephalosporin Analogs Against Microorganisms Determination of Minimum Inhibitory Concentrations The screening experiments in vitro were carried out for antibacterial activities of the phloroglucide analogs II–VII, XII–XIV, bifunctional cephalosporins VIII and IX, as well as 7-(phloroglucidamido)cephalosporins X and XI. Cephalosporins XV and XVI were used as the reference compounds. The lowest concentrations of antibiotics needed for prevention of visible growth of microorganisms; reported as the average values of duplicate determinations. Minimum inhibitory concentrations (MIC) values obtained by use of an agar dilution method whereby organisms were deposited onto medicated agar plates by the replication device of Steers et al [Steers, F. et al. *Antibiot. Chemother.* 1959, 9, 307].

TABLE 1

Minimum Inhibitory Concentrations (µg/mL) of Phloroglucide and Cephalosporin Analogs Against Microorganisms

| compound | S. aureus FDA 209P | S. aureus 95[a,b] | C. albicans | Ps. aerureus 1101-75 | Ps. acrureus 18S-HD[a] |
|---|---|---|---|---|---|
| II | 0.86 | 0.43 | 1.43 | 0.02 | 0.10 |
| III | 3.67 | 0.98 | 3.70 | 0.17 | 0.26 |
| IV | 2.98 | 4.65 | 117.43 | 1.25 | 1.56 |
| V | 14.69 | 15.32 | 125.30 | 5.78 | 4.30 |
| VI | 7.35 | 6.63 | 114.20 | 3.28 | 4.70 |
| VII | 18.15 | 17.76 | 119.56 | 6.03 | 8.32 |
| VIII | 0.41 | 1.20 | 5.86 | 0.98 | 1.24 |
| IX | 0.90 | 2.10 | 6.47 | 1.37 | 3.13 |
| X | 0.35 | 0.28 | 28.31 | 0.28 | 0.45 |
| XI | 0.78 | 0.45 | 14.23 | 0.79 | 0.38 |
| XII | 1.20 | 0.58 | 2.06 | 0.070 | 0.18 |
| XIII | 3.25 | 4.15 | 16.51 | 0.86 | 1.32 |
| XIV | 18.25 | 22.18 | 19.12 | 2.54 | 3.06 |

TABLE 1-continued

Minimum Inhibitory Concentrations (µg/mL) of Phloroglucide and Cephalosporin Analogs Against Microorganisms

| compound | S. aureus FDA 209P | S. aureus 95[a,b] | C. albicans | Ps. aerureus 1101-75 | Ps. acrureus 18S-HD[a] |
|---|---|---|---|---|---|
| XV | 0.70 | >145 | >145 | >145 | >145 |
| XVI | 1.70 | 40.60 | >145 | 69.86 | 135 |

[a]β-Lactamase-producing organism.
[b]Methicillin resistant organism.

EXAMPLE 2

Determination of Minimum Protective Concentrations of Cephalosporin Analogs Against β-Lactamases Determination of Minimum Protective Concentrations The β-lactamase inhibitory properties of cephalosporin-hloroglucide esters VIII and IX as well as 7-(phloroglucidamido)cephalosporins X and XI were studied. Cephalosporins XV and XVI as well as clavulanic acid (XVII) were used in vitro as the reference compound. The average values of duplicate determinations and the ability of compounds to inhibit the hydrolysis of 3-[E-(2,4-dinitro)styryl]-(6R,7R)-7-(2-thienylacetamido)-3-cephem-4-carboxylic acid by β-lactamases from *S. aureus* 95 and *Ps. aeruginosa* 18S-H. Minimum protective concentrations (MPC) values were determined by the procedure of O'Callaghan et al. [O'Callaghan C. H. et al. *Antimicrob. Agents Chemother.* 1972, 1, 283] and are the lowest concentrations of β-lactams needed to protect the indicator from hydrolysis by β-lactamases under standard test conditions within 40 min. The hydrolysis of indicator was evidenced by the appearance of a distinct red color.

TABLE 2

Minimum Protective Concentrations (µg/mL) of Cephalosporin Analogs Against β-Lactamases

| compound[a] | β-lactamase of S. aureus 95 | β-lactamase of Ps. aeruginosa 18S-H |
|---|---|---|
| VIII | 7.08 | 6.74 |
| IX | 4.81 | 5.98 |
| X | 95.20 | 99.78 |
| XI | 88.68 | 93.45 |
| XV | 1.35 | 0.97 |
| XVI | 2.72 | 1.03 |
| XVII | 0.38 | 3.00 |

[a]All compounds were stable (>20 h) in the absence of β-lactamases at 37° C. in a phosphate buffer solution (pH 6.5), except for clavulanic acid (XVII). The β-lactam ring in XVII was destructed within 13 h.

We have successfully synthesized various types of phloroglucide derivatives. Results from their biological assay indicate that cephemphloroglucidic esters acted as effective substrates for β-lactamases of certain bacterial species. Thus their antibacterial spectrum came from phloroglucides liberated from the bifunctional molecules. Moreover, new cephalosporins possessing phloroglucidamide chains attached to the C-7 position showed potent antimicrobial activities and were found resistant to β-lactamases from *S. aureus* 95 and *Ps. aeruginosa* 18S-H. These results has been published in an internationally regarded journal "*J. Med. Chem.* 1997, 40, 3434–3441" October, 1997. We believe that the present invention merits a great potential in the development of new antibacterial agents.

What is claimed is:

1. A phloroglucide derivative having the following formula:

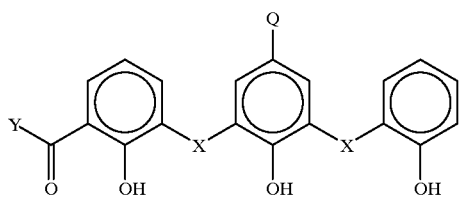
(I)

wherein Q is halogen; X is $CH_2$ or C=O; Y is cephalosporin having a formula of

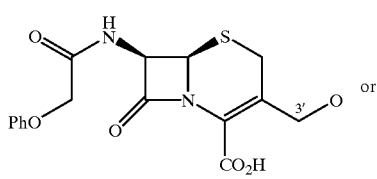
or

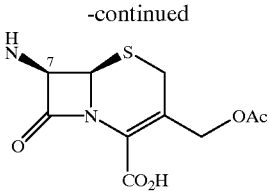

wherein Ph is phenyl, Ac is acetoxy, or pharmaceutically acceptable salts thereof.

2. The phloroglucide derivative according to claim 1, wherein Q is Cl.

3. The phloroglucide derivative according to claim 1, wherein X is $CH_2$.

4. The phloroglucide derivative according to claim 2, wherein X is $CH_2$.

5. An antibacterial pharmaceutical composition comprising a therapeutically effective amount of the phloroglucide derivative as defined in claim 1 or a pharmaceutically acceptable salt thereof, as an active ingredient, in admixture with a pharmaceutically acceptable carrier or diluent for the active ingredient.

6. The pharmaceutical composition according to claim 5, wherein Q is Cl.

7. The pharmaceutical composition according to claim 5, wherein X is $CH_2$.

8. The pharmaceutical composition according to claim 6, wherein X is $CH_2$.

* * * * *